United States Patent [19]

Graas

[11] 4,270,921
[45] Jun. 2, 1981

[54] MICROCHROMATOGRAPHIC DEVICE AND METHOD FOR RAPID DETERMINATION OF A DESIRED SUBSTANCE

[76] Inventor: Joseph E. Graas, 10527 Caminito Glenellen, San Diego, Calif. 92126

[21] Appl. No.: 78,145

[22] Filed: Sep. 24, 1979

[51] Int. Cl.[3] .................... G01N 33/66; G01N 33/72; G01N 31/08; G01N 21/00
[52] U.S. Cl. ................................. 23/230 B; 210/656; 210/198.2; 422/70; 422/72
[58] Field of Search .................. 23/230 B; 422/70, 72; 210/31 C

[56] References Cited

U.S. PATENT DOCUMENTS

| 3,953,172 | 4/1976 | Shapiro | 422/72 X |
| 4,142,858 | 3/1979 | Acuff | 422/70 X |
| 4,168,147 | 9/1979 | Acuff | 422/70 X |

OTHER PUBLICATIONS

R. E. Davis et al., The Lancet, 350-351, Aug. 12, 1978.

Primary Examiner—Sidney Marantz
Attorney, Agent, or Firm—Jackson, Jones & Price

[57] ABSTRACT

A combination of a microcolumn packed with a suitable absorbent material and a centrifuge tube. A predetermined volume of an eluent being capable of selectively eluting a desired substance through the microcolumn is contained above the packing of the absorbent material. The microcolumn and the centrifuge tube are dimensioned in such a manner that upon centrifugation of the predetermined volume of the eluent through the microcolumn, a level of the eluent remaining in the microcolumn, and a level of the eluent in the centrifuge tube coincide substantially at or above a top surface of the packing of the absorbent material. Consequently, centrifugation of the assembly of the microcolumn and the centrifuge tube causes passage of the predetermined volume of eluent through the microcolumn. Determination or assay of the selectively eluted desired substance may be performed by spectrophotometric methods. The device and method is particularly adapted for the determination or assay of a relative concentration of glycosylated hemoglobin species present in the red blood cells of a specific person.

32 Claims, 5 Drawing Figures

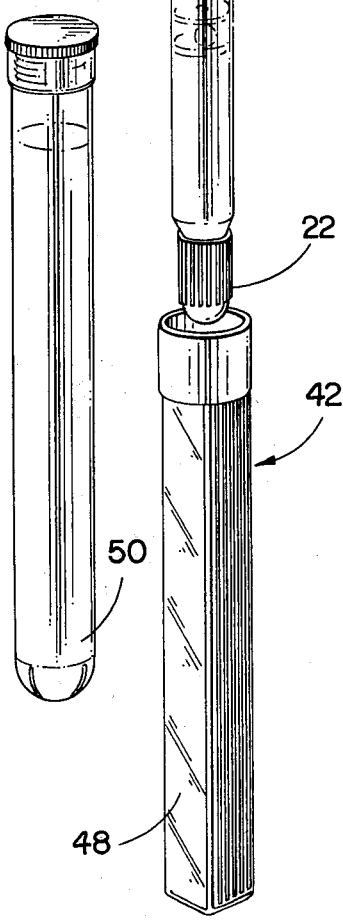

MICROCHROMATOGRAPHIC DEVICE AND METHOD FOR RAPID DETERMINATION OF A DESIRED SUBSTANCE

BACKGROUND OF THE INVENTION

1. Field of the Invention

The present invention is directed to a microchromatographic device adapted for determination of a desired substance through rapid elution from a microcolumn, and particularly adapted for rapid determination of a relative concentration of glycosylated hemoglobin species in a red blood cell lysate of a person. The present invention is also directed to a method for rapid and reliable determination of the relative concentration of glycosylated hemoglobins in the red blood cell lysate of a person.

2. Brief Description of the Prior Art

It has been known in the prior art that several, chromatographically separable minor hemoglobin species are present in the red blood cell lysate of human beings. Glycosylated minor hemoglobin species customarily designated $HB-A_{1a}$, $Hb-A_{1b}$ and $Hb-A_{1c}$ are believed to be Amadori rearranged Shiff base type condensation products of glucose and hemoglobin, wherein a hexose derived from glucose is attached to an N-terminal amino acid in the $\beta$ peptide chain of hemoglobin. The reaction between glucose and the N-terminal amino acid is understood to be practically irreversible under physiological conditions. Therefore within the average 120 day life span of human red blood cells the relative concentration of glycosylated hemoglobin species when compared to non-glycosylated hemoglobin species provides a good numerical indication of the time averaged blood sugar level of a person. Stated differently, the relative concentration of glycosylated hemoglobin species in the red blood cell lysate of a person acts as a numerical index of the cumulative blood sugar history of the person for the preceding 3–4 month time period.

For a detailed description of the chemical nature of glycosylated hemoglobins and their diagnostic significance particularly in monitoring patients suffering from diabetes mellitus, reference is made to the following publications: Kenneth H. Gabbay, Karen Hasty, Jan L. Breslow, R. Curtis Ellison, H. Franklin Bunn, and Paul M. Gallop; Glycosylated Hemoglobins and Long-Term Blood Glucose Control in Diabetes Mellitus, Journal of Clinical Endocrinology and Metabolism, Volume 44 pages 859–864 (1977); H. Franklin Bunn, David N. Haney, Steven Kamin, Kenneth H. Gabbay and Paul M. Gallop: The Biosynthesis of Human Hemoglobin $A_{1c}$ Slow Glycosylation of Hemoglobin in Vivo, The Journal of Clinical Investigation, volume 57, pages 1652–1659 (1976).

In recognition of the practical diagnostic significance of determining the relative glycosylated hemoglobin concentration of red blood cell lysates obtained from patients, the prior art has developed a plurality of microchromatographic techniques and devices for conducting such determinations.

These techniques and devices involve a miniature or microcolumn having a packing of a suitable ion exchange resin. A sample of hemolysed red blood cells taken from a specific person is placed on a top end of the microcolumn, and a first buffer solution is passed through the microcolumn. The first buffer solution is chosen to selectively elute glycosylated hemoglobin species only, while nonglycosylated hemoglobin species stay adhered to the ion exchange resin in the microcolumn. A first numerical value proportional to the concentration of the glycosylated hemoglobin species in the collected eluate of the first buffer is determined spectrophotometrically.

In order to determine a second numerical value proportional to the sum of the concentration of glycosylated and nonglycosylated hemoglobin species in the hemolysate of the specific person, the prior art has employed two alternative approaches. According to a first approach, a second buffer solution is used to elute from the microcolumn the nonglycosylated hemoglobin species, and a third numerical value proportional to its concentration is determined spectrophotometrically. Summation of the first and third numerical values provides the second numerical value. According to a second approach, red blood cells of the patient are lysed in a sample separate from the microcolumn, and the second numerical value is determined spectrophotometrically, after appropriate dilution if necessary, in that sample. A simple ratio of the first and second numerical values, taking dilutions into account if applicable, expressed in a percentage form provides the diagnostic number or index which is characteristic of the history of the patient's blood sugar level.

U.S. Pat. Nos. 4,142,855; 4,142,856; 4,142,857 and 4,142,858 and the publication: Rapid Estimation (2½ Hours) of Glycosylated Hemoglobin for Routine Purposes by P. A. Kynock and H. Lehmann, *The Lancet* July 2, 1977 pages 16–17, are exemplary of the above summarized microchromatographic techniques and devices. These patents and the publication describe the specific nature and parameters of the materials used in the techniques.

As it is readily appreciated by those skilled in the diagnostic arts, routine diagnostic determinations performed in a laboratory of a clinic or hospital should preferably be completed in a time span of minutes rather than hours. Furthermore, diagnostic measurements strive for increasing accuracy and reliability.

In this regard, it is noted that the prior art techniques of determining the diagnostic number or index characteristic of the history of the blood sugar level of a person are, generally speaking, quite temperature dependent. In other words, reproducibility of the results is impaired if several measurements are not conducted at essentially identical temperatures.

An article authored by R. E. Davis and D. J. Nicol titled "A Rapid Simplified Method for Routine Measurement of Glycosylated Hemoglobin," *The Lancet* Aug. 12, 1978 pages 350–351, describes a microchromatographic method wherein a buffer solution capable of eluting the glycosylated hemoglobin species from the microcolumn is rapidly forced through the microcolumn in a centrifugation step. As a result, the diagnostic measurement is said to be completed in approximately 5 minutes.

In another effort to simplify the diagnostic glycosylated hemoglobin determination procedures, a diagnostic microcolumn was recently made commercially available in the United States wherein lysis of the red blood cells is performed in an upper reservoir of the microcolumn rather than in a separate vessel.

In spite of the above described advances in the prior art, there is still significant room for improvement to render these diagnostic determinations easier to perform, faster and less temperature dependent. The present invention provides such a technique and a microchromatographic device to perform the technique.

SUMMARY OF THE INVENTION

It is an object of the present invention to provide a microchromatographic device and method for the determination of a numerical index characteristic of the history of blood sugar level of a person which permit fast and efficient performance of the determination in a minimum number of steps.

It is another object of the present invention to provide a microchromatographic method for the determination of a numerical index characteristic of the history of the blood sugar level of a person which is substantially independent of temperature at least in a given temperature range.

It is still another object of the present invention to provide a rapid microchromatographic device and method wherein a volume of an eluent passing through a microcolumn is automatically controlled in a centrifugation step.

These and other objects and advantages are attained by a microchromatographic device which comprises a combination of an appropriately dimensioned microcolumn and an appropriately dimensioned centrifuge tube. The microcolumn contains in an intermediate portion thereof a packing of a suitable absorbent material.

A liquid sample containing a desired substance to be measured, is placed into the column. The column contains a volume of a suitable eluent, the volume of the eluent or a portion thereof being sufficient to elute the desired substance through the microcolumn. The microcolumn is positioned upright in the centrifuge tube and the assembly of the microcolumn and of the centrifuge tube is subjected to a centrifugal force. The dimensions of the centrifuge tube and of the microcolumn are selected in such a manner that when a predetermined volume of the eluent required for eluting the desired substance passes through the microcolumn, a level of the eluate in the centrifuge tube and a level of the eluent remaining in the microcolumn coincide above a top surface of the absorbent packing of the microcolumn. Consequently, further centrifugation fails to pass more eluent through the microcolumn.

When the microchromatographic device is applied for determination of a diagnostic numerical index of the history of the blood sugar level of a person, the absorbent packing is an ion exchange resin, the eluent is a buffer containing a lysing agent and the desired substance is a glycosylated hemoglobin species which is measured spectrophotometrically. A total hemoglobin species concentration is measured spectrophotometrically in a different sample of lysed red blood cells of the same person. The diagnostic numerical index is calculated according to a known formula from said measurements taking dilutions and the like into account.

The several features of the present invention can be best understood, together with further objects and advantages, by reference to the following description, taken in connection with the accompanying drawings.

DESCRIPTION OF THE PREFERRED EMBODIMENTS

The following specification taken in conjunction with the drawings sets forth the preferred embodiments of the present invention in such a manner that any person skilled in the chemical arts and particularly in the art of clinical chemistry can use the invention. The embodiments of the invention disclosed herein are the best modes contemplated by the inventor for carrying out his invention in a commercial environment, although it should be understood that various modifications can be accomplished within the parameters of the present invention.

Figure 1:
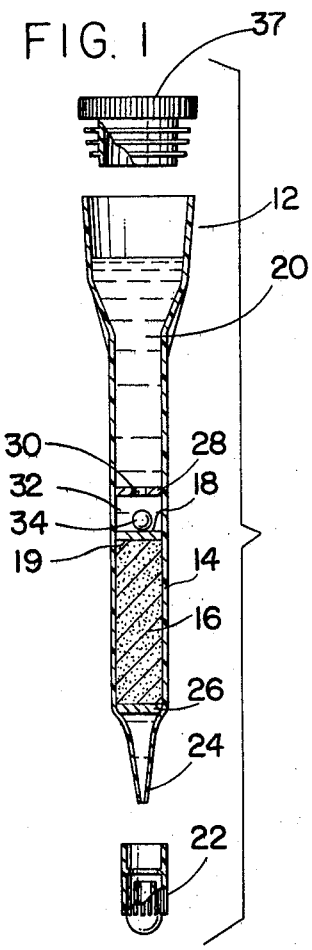
FIG. 1 is a partially exploded cross sectional view of a first preferred embodiment of a microcolumn comprising a part of the microchromatographic device of the present invention.
Figure 3:
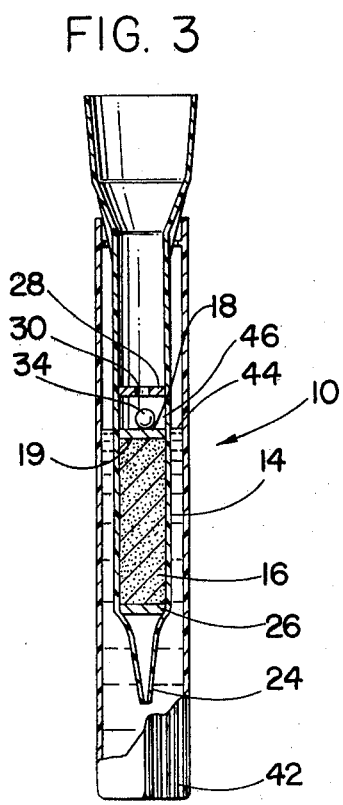
FIG. 3 is a cross sectional view of the first preferred embodiment of the microchromatographic device of the present invention, the view showing respective levels of an eluent and an eluate in the microcolumn and in a centrifuge tube, after a centrifugation step.

Referring now to the drawing figures and particularly to the cross sectional view of FIGS. 1 and 3, a first preferred embodiment of the microchromatographic device 10 of the present invention is disclosed. The microchromatographic device 10 includes a microcolumn 12, which has an intermediate portion 14 filled with a packing 16 of a suitable absorbent material.

It is noted at the outset of the present description that the herein described microchromatographic device 10 is ideally suited for the determination of a diagnostic numerical index or indicator which is characteristic of the history of the blood sugar level of a specific person. Nevertheless, other microchromatographic applications of the herein described device 10 are possible particularly in the clinical diagnostic field. One such readily apparent application is for the clinical diagnostic determination of catechol amines. In light of this, although the ensuing description is specifically directed to the determination of the above mentioned diagnostic number or index characteristic of time averaged blood sugar levels, it should be borne in mind that the herein disclosed generic principles may be readily adapted for other microchromatographic measurements and processes.

Referring again to FIGS. 1 and 3, the packing 16 of the absorbent material in the intermediate portion 14 of the microcolum 12 comprises an ion exchange resin. The ion exchange resin is capable of separating glycosylated hemoglobin species present in the lysate of human red blood cells from nonglycosylated hemoglobin species. More specifically, the ion exchange resins used in accordance with the present invention for the separation of glycosylated hemoglobins, exhibit in their operating pH range less affinity for binding glycosylated hemoglobins than nonglycosylated hemoglobins. For the general principles utilized in the determination of a relative concentration of glycosylated hemoglobins, reference is made to the introductory part of the present application, and to U.S. Pat. Nos. 4,142,855; 4,142,856; 4,142,857 and 4,142,858. These patents describe examples of specific ion exchange resins, buffer solutions and other materials which can be used for the microchromatographic determination of the diagnostic numerical index or indicator. The specifications of U.S. Pat. Nos. 4,142,855; 4,142,856; 4,142,857 and 4,142,858 are hereby expressly incorporated by reference.

An ion exchange resin which is most preferred for use in the present invention is a copolymer of methacrylic acid and divinylbenzene containing negatively charged carboxyl groups. This resin is equilibrated prior to the determination or assay in a phosphate buffer of 6.70 pH. The phosphate buffer contains approximately 1% of a saponin type lysing agent such as Triton, and preferably has an ionic strength which results in a conductivity of $6.5 \pm 0.2 \times 10^{-3} \Omega^{-1}$ at 23.5° C.

The above described ion exchange resin is commercially available as CG 50 weak cationic ion exchange resin, 200–400 mesh size. The phosphate buffer is prepared by dissolving in addition to the Triton, 1.18 g of disodium hydrogen phosphate, 4.59 g of sodium dihydrogen phosphate monohydrate, 0.10 g of sodium azide, 0.49 g sodium cyanide and 1.0 g sodium chloride in 1.0 L of distilled or deionized water. Thereafter the pH of the resulting solution is carefully adjusted to 6.70 by addition of either 12 N aqueous hydrochloric acid or 10 N aqueous sodium hydroxide solution, as is necessary. The buffer solution is used for equilibrating the ion exchange resin at pH 6.70 and for transferring the ion exchange resin into the intermediate portion 14 of the microcolumn 12, wherein the ion exchange resin forms the settled packing 16.

Part of the buffer solution permeates the ion exchange resin packing 16, and an additional volume of the buffer solution is contained in the microcolumn 12 above an upper boundary or limit 18 of the packing 16. In the preferred embodiments of the present invention a fritted disk 19 may be disposed immediately above the upper boundary. The additional volume of the buffer solution disposed above the packing 16 bears the reference numeral 20 in the drawing figures. As it is described in more detail below, the additional volume 20 has a particular significance in the practice of the present invention.

Still referring to the drawing FIGS. 1 and 3, a removable stopper or plug 22 which is friction fitted to a lower relatively narrow outlet stem or tube 24 of the microcolumn 12, is disclosed. The packing 16 of the ion exchange resin is supported by a fritted disk 26 or the like which is permeable to liquid but not to the particles of the ion exchange resin. A disk 28 having an aperture 30 in the center thereof is mounted above the upper fritted disk 19 or above the upper limit 18 of the ion exchange resin packing 16, thus defining a chamber 32 between the disk 28 and said upper fritted disk 19. A glass ball 34 is positioned within the chamber 32. A removable second stopper or plug 36 is provided to seal a top end of the microcolumn 12.

Figure 2:
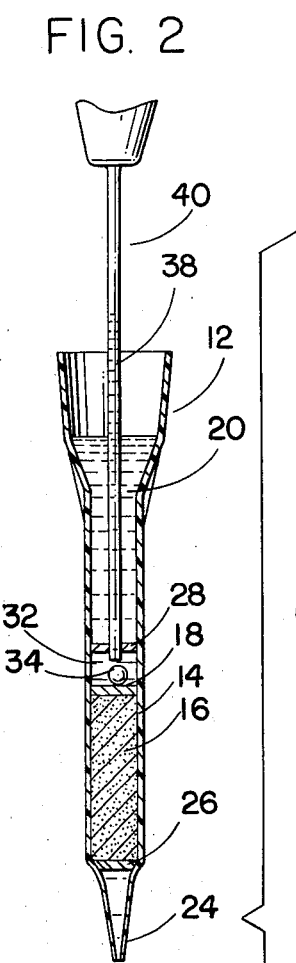
FIG. 2 is a cross sectional view of the first preferred embodiment of the microcolumn, the view showing introduction of a sample into an eluent contained in the microcolumn.

Referring now to FIGS. 1, 2 and 3 and particularly to FIGS. 2 and 3, the microchromatographic device 10 and the practice of the method of the present invention is further specifically described. The second stopper or plug 36 is removed from the microcolumn 12. Alternatively, as in the embodiments described herein the stopper or plug 36 may have an upper seal 37 which is removable. After removal of the seal 37 an aperture (not shown) exists in the plug for the introduction of a sample. Thus a sample 38 of well mixed EDTA oxalated blood is introduced by a suitable dispensing device 40 through the aperture 30 into the chamber 32. The dispensing device is shown only schematically on FIG. 2.

The microcolumn 12 is then slightly shaken or twirled about its vertical axis whereby the glass ball 34 is set in motion and thoroughly mixes the blood sample with the buffer solution contained in the chamber 32. As the blood sample is admixed with the buffer solution, lysis of the red blood cells occurs due to the action of the lysing agent contained in the buffer solution. The lysis is usually complete in approximately one minute or less, and the several hemoglobin species including glycosylated hemoglobins are released into the buffer solution.

It is an important aspect of the present invention that the additional volume 20 of the buffer solution contained above the ion exchange resin packing 16 is carefully chosen to be sufficient to selectively elute the glycosylated hemoglobin species from the ion exchange resin. In this regard, appropriate proportioning of the relative amounts of the blood sample, the ion exchange resin and the additional or predetermined volume 20 of the buffer solution is important. If the first preferred embodiment described here, the volume of the blood sample is 10 microliter, the inner diameter of the intermediate portion 14 of the microcolumn is approximately 0.8 cm, the height of packing is approximately 3 cm, and the additional or predetermined volume of the buffer solution is 4.0 ml.

The flow rate of the microcolumn 12 packed with the ion exchange resin of 200–400 mesh size is such that under the force of gravity only, it takes approximately 1¾–1½ hours to pass 4.0 ml buffer solution through the column. It is of course readily appreciated by those skilled in the art that utilizing a courser mesh resin to significantly increase the flow rate of the microcolumn would adversely affect the ability of the microcolumn 12 to separate glycosylated hemoglobin species from nonglycosylated hemoglobin species.

In order to maintain the separational capability of the microcolumn and yet complete the separation in the time span of approximately one or two minutes, the microcolumn 12 is placed in a centrifuge tube 42. Therein it is supported and held in an upright position as is shown on FIG. 3. Prior to placement of the microcolumn 12 into the centrifuge tube 42 the stopper or plug 22 is removed from the outlet stem or tube 24. In fact, the centrifuge tube 42 may be used to support the microcolumn already while the blood sample is added.

Centrifugation of the assembled microcolumn 12 and centrifuge tube 42 for approximately 2 minutes at 50–1000 g causes the predetermined volume 20 of the buffer solution to pass through the packing 16 of the ion exchange resin and to accumulate in the centrifuge tube 42 as is shown on FIG. 3.

It is another important aspect of the present invention that the relative dimensions of the centrifuge tube 42, and of the microcolumn including the intermediate portion 14 are carefully selected in such a manner that when the predetermined volume of the buffer solution accumulates in the centrifuge tube 42 its level 44 substantially coincides with the level 46 of the buffer solution remaining in the microcolumn 12. Furthermore, the levels 44 and 46 are disposed above or more preferably even with the upper boundary or limit 18 of the packing 16 or with the fritted disk 19, as is shown in FIG. 3. Thus, in the herein described first preferred embodiment, the amount of the buffer solution collected in the centrifuge tube 42 after centrifugation is 4.0 ml, and this amount contains the eluted glycosylated hemoglobins.

It is readily understood that once the levels 44 and 46 are even with one another, further centrifugation fails to force more buffer solution out of the microcolumn 12. Thus, the above described arrangement assures that a correct amount of buffer solution passes through the microcolumn and that the eluted glycosylated hemoglobins are dissolved in the known predetermined volume of the buffer solution.

Experience has shown that if the substantially coinciding liquid levels 44 and 46 were disposed significantly below the upper limit 18 of the packing 16, separation of the glycosylated hemoglobin species from nonglycosylated hemoglobin species would be severely impaired. This would, of course, defeat the purpose of the herein described diagnostic process.

After the centrifugation is completed, concentration of the glycosylated hemoglobin species in the known predetermined volume of the eluted buffer solution is assayed spectrophotometrically. In the first preferred embodiment of the microchromatographic device 10 of the present invention, the centrifuge tube 42 is adapted to serve as a cuvette in the spectrophotometric assay. As is shown on the perspective view of FIG. 5, the centrifuge tube 42 has at least two parallel wall surfaces 48 which are transparent to visible light at least in the 400–430 nm range. As a result, the spectrophotometric measurement of the glycosylated hemoglobin species at approximately 415 nm according to standard practice in the art may be conducted without transferring the eluate from the centrifuge tube 42 into another cuvette (not shown).

Figure 5:
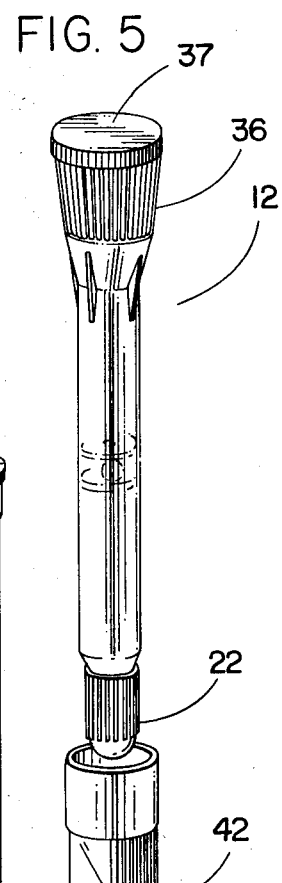
FIG. 5 is a perspective view of the first preferred embodiment of the microchromatographic device of the present invention, the view showing a separate vessel wherein a lysate of red blood cells may be prepared for measurement of total hemoglobin species concentration.

Still referring to the perspective view of FIG. 5, a vessel substantially in the shape of a test tube 50, is shown. In the practice of the present invention, the vessel or test tube 50 may be provided together with the microcolumn 12 and centrifuge tube 42 to form a substantially integrated diagnostic kit. The vessel 50 contains a premeasured volume of the same buffer solution which is provided in the microcolumn 12.

A sample of the blood of the person is then added to the vessel 50. Due to the action of the lysing agent contained in the buffer solution, both glycosylated and nonglycosylated hemoglobin species are released from the red blood cells into the buffer solution. Concentration of the combined hemoglobin species contained in the vessel is then assayed spectrophotometrically at approximately 415 nm according to standard practice of the art.

In the first preferred embodiment of the microchromatographic device 10 described here, the vessel 50 contains 14 ml of the buffer solution. This relatively large volume of the buffer solution provides an advantage in that the combined hemoglobin species can be assayed spectrophotometrically without further dilution. The different dilutions of the blood samples introduced into the microcolumn 12 and the vessel 50 must, however, be taken into account when calculating a relative concentration of the glycosylated hemoglobin species versus the total or combined hemoglobin species. The relative concentration, when expressed in a percentage form comprises the diagnostic numerical index or indicator which is characteristic of the history of the blood sugar level of the person. A detailed description of the spectrophotometric assaying process and description of the calculation to determine the percentagewise relative concentration is not provided here because these matters lie well within the state of the art.

As an additional feature of the present invention, it has been found that more reliable results are obtained when the step of eluting or passing the buffer solution through the packing of the ion exchange resin is conducted at a lower than usual temperature, preferably in the temperature range of $-5°-12°$ C. It has been found in accordance with the present invention that in the temperature range of $-5°-12°$ C. results of the assays are substantially independent of the actual temperature at which the assay is performed. Furthermore, performing the determinations or assays in this temperature range provides more reliable and reproducible results even if a prior art microchromatographic column is used. Thus, even if the buffer solution passes through the packing of the ion exchange resin merely under the force of gravity more reliable results are obtained if the elution step is conducted between $-5°-12°$ C.

As is well appreciated by those skilled in the art, in order to obtain the more reliable results the elution step may be performed in a cold room wherein the ambient temperature is customarily maintained at approximately 5° C. A very convenient way to perform the elution step in the desired lowered temperature range is to store the microcolumn 12 in a refrigerator of 2°–6° C. for several hours. After the microcolumn 12 is removed from the refrigerator the determination or assay is performed immediately, at least up to completion of the elution step, before the microcolumn 12 reaches ambient temperature. Experience has shown that reliable and reproducible results are obtained in this manner.

Tables I and II respectively show the results of several assays of blood samples of two patients. In each table a respective column shows the percentage of glycosylated hemoglobin found and the temperature at which the assay was conducted. It is readily apparent from these tables that between 1°–12° C. and preferably between 1°–9° C. the results are quite temperature independent. Above 12° C. however the temperature dependence of the assays (not shown here) is quite significant.

TABLES I AND II

| TABLE I | | TABLE II | |
| --- | --- | --- | --- |
| Assay of Blood Samples at Different Temperatures SUBJECT "A" | | Assay of Blood Samples at Different Temperatures SUBJECT "B" | |
| %HbA$_1$ | T°C. | %HbA$_1$ | T°C. |
| 5.18% | 2° C. | 7.12% | 2° C. |
| 5.21 | 2 | 7.06 | 2 |
| 4.95 | 3 | 7.84 | 3 |
| 4.62 | 3 | 6.88 | 3 |
| 5.18 | 4 | 8.18 | 4 |
| 5.21 | 4 | 8.45 | 4 |
| 5.24 | 5 | 8.04 | 5 |
| 5.24 | 5 | 7.97 | 5 |
| 5.34 | 6 | 7.63 | 6 |
| 5.01 | 6 | 8.08 | 6 |
| 5.84 | 7 | 8.62 | 7 |
| 5.67 | 7 | 8.52 | 7 |
| 5.87 | 8 | 8.79 | 8 |
| 5.58 | 8 | 8.76 | 8 |
| 5.58 | 9 | 8.86 | 9 |

TABLES I AND II-continued

| TABLE I | | TABLE II | |
|---|---|---|---|
| Assay of Blood Samples at Different Temperatures SUBJECT "A" | | Assay of Blood Samples at Different Temperatures SUBJECT "B" | |
| %HbA$_1$ | T°C. | %HbA$_1$ | T°C. |
| 5.64 | 9 | 8.72 | 9 |
| 5.87 | 10 | 8.72 | 10 |
| 5.90 | 10 | 8.79 | 10 |
| 5.94 | 11 | | |

Figure 4:
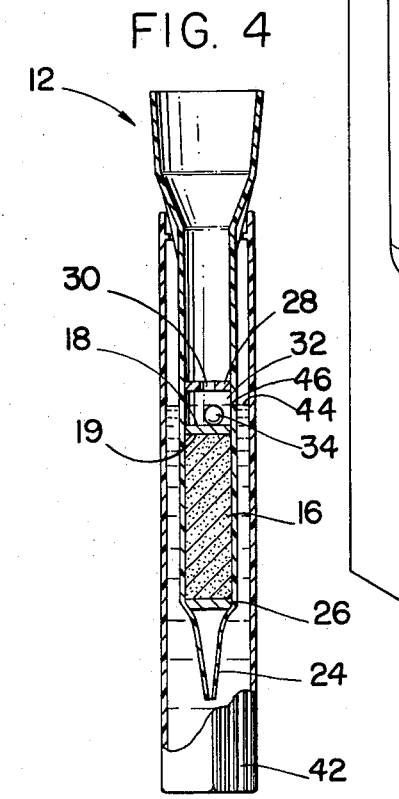
FIG. 4 is a cross sectional view of a second preferred embodiment of the microchromatographic device of the present invention, the view showing respective levels of the eluent and the eluate in the microcolumn and in the centrifuge tube after a centrifugation step.

Referring now briefly to FIG. 4, a second preferred embodiment of the microchromatographic device 10 of the present invention is disclosed. In the second preferred embodiment the predetermined volume of the buffer solution is selected in such a manner that after centrifugation the level 44 of the eluted buffer solution in the centrifuge tube 42 is significantly above the upper limit 18 of the ion exchange resin packing 16. The level 46 of the buffer solution remaining in the microcolumn 12 coincides, in accordance with the present invention, with the level 44. In this embodiment prior to the centrifugation step more buffer solution is contained above the packing 16 than the predetermined volume required for elution of the glycosylated hemoglobin species through the ion exchange column. In performing the calculations, however, the fact that some of the introduced glycosylated hemoglobin remains in the buffer solution above the packing 16 even after the centrifugation step, must be taken into consideration.

What has been described above is a microchromatographic device and method for rapid and reproducible determination of a diagnostic numerical index characteristic of the history of the blood sugar level of a person. Furthermore, the microchromatographic device is readily adaptable for application in other microchromatograph assays and determinations wherein a predetermined volume of an eluent must be passed through a microcolumn in a short period of time. Several modifications of the present invention may become readily apparent to those skilled in the art in light of the present teachings. Accordingly, the scope of the present invention should be interpreted solely from the following claims.

What is claimed is:

1. A microchromatographic device for use in a rapid quantitative measurement of a desired substance, the device comprising the combination of:

a microcolumn having exterior walls and containing a packing of a set amount of absorbent material, said absorbent material being contained within a predetermined intermediate portion of the microcolumn, the microcolumn containing space for accommodating liquid above an upper boundary of the intermediate portion of the microcolumn;

an eluent contained in the microcolumn, a first part of the total volume of the eluent permeating the packing of the absorbent material and being contained in the intermediate portion of the microcolumn, a second part of the eluent comprising the remainder of the total volume of the eluent, said second part of the eluent being contained in the space above the intermediate portion of the microcolumn and including a predetermined volume which is capable of selectively eluting the desired substance from the absorbent material, the second part of the eluent being at least as much as the predetermined volume of the eluent;

means located on the microcolumn below the intermediate portion for sealing the packing of absorbent material in the microcolumn but allowing for outflow of the eluent from the microcolumn at the option of an operator, and a centrifuge tube having inner walls, the microcolumn being at least partially inserted into the centrifuge tube wherein it is removably but fixedly held in an upright position, a void space being disposed between the inner walls of the centrifuge tube and the exterior walls of the microcolumn, a portion of the void space equalling in volume the predetermined volume of the eluent; the relative dimensions of the microcolumn, of the intermediate portion of the microcolumn, of the centrifuge tube, and of the second part of the total volume of the eluent being selected in such a manner that upon passage of the predetermined volume of the eluent through the microcolumn into the centrifuge tube the level of eluent in the centrifuge tube coincides with the level of the eluent remaining in the microcolumn, said level being disposed not substantially lower than the upper boundary of the intermediate portion of the microcolumn wherein the absorbent material is contained, whereby a centrifugation of the assembled microcolumn and centrifuge tube causes the passage of the predetermined volume of the eluent into the centrifuge tube and whereby the desired substance is eluted from the absorbent material into the centrifuge tube and said desired substance is dissolved in the predetermined volume of the eluent.

2. The microchromatographic device of claim 1 wherein the second part of the total volume of the eluent equals the predetermined volume of the eluent, and wherein after passage of the predetermined volume of the eluent through the microcolumn the level of the eluent in the centrifuge tube and the level of the eluent in the microcolumn substantially coincide with the upper boundary of the intermediate portion of the microcolumn.

3. The microchromatographic device of claim 1 wherein the microcolumn includes a disk located above the upper boundary of the intermediate portion, the disk and the upper boundary defining a mixing chamber, said disk being provided with means for allowing passage of a sample through the disk into the mixing chamber.

4. The microchomatographic device of claim 3 wherein a mixing member is permanently positioned within the chamber, said mixing member being actuated by shaking and like agitation of the microcolumn.

5. The microchromatographic device of claim 3 wherein the means for allowing passage of a sample comprises an aperture located in the disk, and wherein the mixing member is a ball composed of an inert material.

6. The microchromatographic device of claim 5 wherein the absorbent material is an ion exchange resin and the eluent is an aqueous buffer solution.

7. The microchromatographic device of claim 6 wherein the centrifuge tube is adapted for use as a cuvette for directly measuring concentration of the desired substance in the predetermined volume of the eluent by one of ultraviolet and visible spectrophotometric means.

8. The microchromatographic device of claim 1 wherein the centrifuge tube is adapted for use as a cuvette for directly measuring concentration of the desired substance in the predetermined volume of the eluent by one of ultraviolet and visible spectrophotometric means.

9. A microchromatographic device for use in a rapid quantitative determination of a numerical value as a diagnostic indicator of the blood sugar condition of a specific person, the device comprising the combination of:
- a microcolumn having exterior walls and containing a packing of a set amount of ion exchange resin, said ion exchange material being contained within a predetermined intermediate portion of the microcolumn, the microcolumn containing space for accomodating liquid above an upper boundary of the intermediate portion of the microcolumn;
- an aqueous buffer solution contained in the microcolumn, a first part of the total volume of the buffer solution permeating the packing of the ion exchange resin and being contained in the intermediate portion of the microcolumn, a second part of the buffer solution comprising the remainder of the total volume of the buffer solution and and being contained in the space above the intermediate portion of the microcolumn, said second part of the buffer solution including a predetermined volume which is capable of selectively eluting a glycosylated hemoglobin species from the ion exchange resin, the second part of the buffer solution being at least as much as the predetermined volume of the buffer solution;
- means located on the microcolumn below the intermediate portion for sealing the packing of ion exchange resin in the microcolumn but allowing for outflow of the buffer solution from the microcolumn at the option of an operator, and
- a centrifuge tube having inner walls, the microcolumn being at least partially inserted into the centrifuge tube wherein it is removably but fixedly held in an upright position, a void space being disposed between the inner walls of the centrifuge tube and the exterior walls of the microcolumn, a portion of the void space equalling in volume the predetermined volume of the buffer solution; the relative dimensions of the microcolumn, of the intermediate portion of the microcolumn, of the centrifuge tube, and of the second part of the total volume of the buffer solution being adjusted in such a manner that upon passage of the predetermined volume of the buffer solution through the microcolumn into the centrifuge tube the level of the buffer solution in the centrifuge tube substantially coincides with the level of the buffer solution remaining in the microcolumn, said level being disposed not substantially lower than the upper boundary of the intermediate portion of the microcolumn wherein the ion exchange resin is contained, whereby a centrifugation of the assembled microcolumn and centrifuge tube causes the passage of the predetermined volume of the buffer solution into the centrifuge tube, and whereby the glycosylated hemoglobin species is eluted from the ion exchange resin into the centrifuge tube and said glycosylated hemoglobin species is dissolved in the predetermined volume of the buffer solution.

10. The microchromatographic device of claim 9 wherein the second part of the total volume of the buffer solution equals the predetermined volume of the buffer solution, and wherein after passage of the predetermined volume of the buffer solution through the microcolumn the level of the buffer solution in the microcolumn and the level of the buffer solution in the centrifuge tube substantially coincides with the upper boundary of the intermediate portion of the microcolumn.

11. The microchromatographic device of claim 10 wherein the microcolumn includes a first disk having means for allowing passage of a sample of red blood cells therethrough, and a second fritted disk immediately above the upper boundary of the intermediate portion of the microcolumn, said first and second disks defining a mixing chamber.

12. The microchromatographic device of claim 11 wherein a mixing member is permanently positioned within the chamber, said mixing member being actuated by shaking and like agitation of the microcolumn.

13. The microchromatographic device of claim 12 wherein the mixing member is a ball made of an inert material.

14. The microchromatographic device of claim 12 wherein the means for allowing passage of a sample comprises an aperture located in the first disk.

15. The microchromatographic device of claim 12 wherein the means for sealing the microcolumn and for allowing outflow of the buffer solution comprises a removable cap friction fitted upon a narrow portion of the microcolumn.

16. The microchromatographic device of claim 12 wherein a top end of the microcolumn is sealed by a removable plug.

17. The microchromatograhic device of claim 12 wherein the centrifuge tube is adapted for serving as a cuvette in the 400–430 nm range for spectrophotometric determination of the glycosylated hemoglobin species whereby after passage of the predetermined volume of buffer solution the concentration of the glycosylated hemoglobin species may be spectrophotometrically measured without transferring the buffer solution from the centrifuge tube.

18. A device for use in a rapid quantitative determination of a numerical value as a diagnostic indicator of the blood sugar condition of a specific person, the device comprising the combination of:
- a microcolumn;
- a settled packing of an ion exchange resin confined in the microcolumn, the settled packing substantially having an upper limit;
- a buffer solution contained within the microcolumn permeating through the packing of the ion exchange resin and having an additional predetermined volume disposed above the upper limit of the packing, the predetermined volume capable of selectively eluting a glycosylated hemoglobin species through the packing of the ion exchange resin;
- a lysing agent dissolved in the buffer solution capable of lysing whole human red blood cells and releasing the glycosylated hemoglobin species and non-glycosylated hemoglobin species therefrom;
- means located below the packing of the ion exchange resin for shutting the flow of the buffer solution through the microcolumn and for allowing said flow at the option of an operator;

a centrifuge tube adapted for receiving the microcolumn and for holding the same in an upright position, a void space being disposed between interior walls of the centrifuge tube and exterior walls of the microcolumn, the void space being large enough to accommodate the predetermined volume of the buffer solution, the relative dimensions of the centrifuge tube and of the microcolumn including the packing of the ion exchange resin being selected in such a manner that upon passage of the predetermined volume of buffer solution through the microcolumn into the centrifuge tube the level of the buffer solution in the centrifuge tube and in the microcolumn substantially coincide with the limit of the settled packing of the ion exchange resin whereby after an introduction of a sample of red blood cells into the predetermined volume of the buffer solution the glycosylated hemoglobin species is released therefrom by the lysing agent, and whereby after centrifugation of the assembled microcolumn and centrifuge tube only the predetermined volume of buffer solution passes through the microcolumn eluting the glycosylated hemoglobin species which is contained in said predetermined volume.

19. The device of claim 18 wherein the centrifuge tube is adapted for serving as a cuvette for spectrophotometric measurement substantially at 415 nm whereby a numerical value proportional to the concentration of the glycosylated hemoglobin species present in the predetermined volume of the buffer solution may be directly obtained spectrophotometrically without transferring the buffer solution from the centrifuge tube.

20. The device of claim 18 wherein the combination further comprises a vessel having a second predetermined amount of the buffer solution therein, said buffer solution also containing the lysing agent, whereby introduction of a sample of whole red blood cells into the vessel and subsequent spectrophotometric measurement substantially at 415 nm provides a numerical value proportional to the sum of glycosylated and nonglycosylated hemoglobin species present in the second predetermined volume.

21. The device of claim 18 wherein a disk having an aperture is disposed in the microcolumn above the upper limit of the settled packing of ion exchange resin, said upper limit and said disk defining a mixing chamber, the aperture allowing introduction of a sample of the whole red blood cells into the mixing chamber.

22. The device of claim 21 wherein a mixing member is contained in the mixing chamber, said mixing member being actuated by slight agitation of the microcolumn.

23. The device of claim 22 wherein the ion exchange resin in a copolymer of methacrylic and divinylbenzene containing negatively charged carboxyl groups, said ion exchange resin having been equilibrated at pH 6.70, and wherein the buffer solution has a pH of 6.70.

24. The device of claim 23 wherein the buffer solution is a phosphate buffer having a conductivity of $6.5 \pm 0.2 \times 10^{-3} \Omega^{-1}$ at 23.5° C.

25. A method for rapid quantitative determination of a first numerical value as a diagnostic indicator of a cumulative blood sugar condition of a specific person, the method comprising the steps of:

introducing a sample of whole red blood cells into a top portion of a microcolumn having an intermediate portion which is packed with an ion exchange resin, the ion exchange resin being permeated by a first part of a first buffer solution having a lysing agent dissolved therein, the top portion of the microcolumn containing a second part of the first buffer solution, allowing the lysing agent to break up the whole red blood cells and to release therefrom glycosylated hemoglobin species and nonglycosylated hemoglobin species, the ratio of the glycosylated and nonglycosylated hemoglobin species being indicative of the cumulative blood sugar condition of the specific person;

positioning the microcolumn into a centrifuge tube;

subjecting the microcolumn to a centrifugal force of 50-1000 g thereby forcing a predetermined volume of the first buffer solution to pass from the top portion of the microcolumn through the ion exchange resin and to be discharged into the centrifuge tube, at least the predetermined volume of the first buffer solution being originally included in the second part of the first buffer solution and being originally contained in the top portion of the microcolumn, the predetermined volume of the first buffer solution reaching a level in the centrifuge tube which coincides with the level of the first buffer solution remaining in the centrifuge tube, said level being positioned in the microcolumn at least as high as a top surface of the ion exchange resin packing whereby further centrifugation fails to force more of the first buffer solution to pass through the ion exchange resin into the centrifuge tube; the first buffer solution and the ion exchange resin further being selected so that the predetermined volume of the first buffer solution selectively elutes the glycosylated hemoglobin species through the ion exchange resin;

spectrophotometrically measuring in the eluted predetermined volume of the first buffer solution a second numerical value proportional to the concentration of glycosylated hemoglobin species therein, and preparing a sample of lysed red blood cells of the same specific person in a second buffer solution of the same composition as the first buffer solution and spectrophotometrically measuring a third numerical value proportional to the sum of glycosylated and nonglycosylated hemoglobin species in the second buffer solution, said first numerical value being calculated from the second and third numerical values.

26. The method of claim 25 further comprising the step of mixing the introduced sample of whole red blood cells with the first buffer solution contained in the top portion of the microcolumn.

27. The method of claim 25 wherein said steps of introducing, allowing, positioning and subjecting are conducted while the temperature of the microcolumn and of the ion exchange resin and the first buffer solution contained therein is in the 0°-12° C. range.

28. The method of claim 27 wherein the ion exchange resin is a copolymer of methacrylic acid and divinylbenzene containing negatively charged carboxyl groups, and wherein the first buffer solution is a phosphate buffer having a pH of 6.70.

29. The method of claim 25 wherein the ion exchange resin is a copolymer of methacrylic acid and divinylbenzene containing negatively charged carboxyl groups, said ion exchange resin having been equilibrated at pH 6.70, and wherein the first buffer solution is a phosphate buffer of pH 6.70 having a conductivity of $6.5\pm0.2\times10^{-3}\Omega^{-1}$ at 23.5° C.

30. In a method for the determination of a first numerical value as a diagnostic indicator of a cumulative blood sugar condition of a specific person, said method including the steps of selectively eluting with a buffer solution a hemolysate of red blood cells of the specific person through a microcolumn of an ion exchange resin, collecting an eluate and spectrophotometricaly determining a second numerical value which is proportional to the concentration of a glycosylated hemoglobin species in said eluate, spectrophotometrically determining a third numerical value in a lysed sample of the red blood cells of the specific person containing both glycosylated and nonglycosylated hemoglobin species, the first numerical value being calculated from the second and third numerical values, the improvement comprising:

conducting the step of elution in a temperature range between $-5°-12°$ C. wherein the first numerical value obtained as a result of said determination is substantially independent of the actual temperature at which the step of elution is conducted.

31. The method of claim 30 wherein the ion exchange resin is a copolymer of methacrylic acid and divinylbenzene containing negatively charged carboxyl groups, and wherein the buffer solution is a phosphate buffer having a pH of 6.70.

32. The method of claim 31 wherein the ion exchange resin has been equilibrated at pH 6.70 and wherein the buffer solution has a conductivity of $6.5\pm0.2\times10^{-3}\Omega^{-1}$ at 23° C.

* * * * *

UNITED STATES PATENT AND TRADEMARK OFFICE
CERTIFICATE OF CORRECTION

PATENT NO. : 4,270,921

DATED : June 2, 1981

INVENTOR(S) : Joseph E. Graas

It is certified that error appears in the above—identified patent and that said Letters Patent is hereby corrected as shown below:

Column 6, line 29 after "important", delete [If] and insert --In--.

Column 6, line 39, delete [178] and insert --1/2--.

Signed and Sealed this

Twenty-seventh Day of October 1981

[SEAL]

Attest:

GERALD J. MOSSINGHOFF

*Attesting Officer*  *Commissioner of Patents and Trademarks*